United States Patent
Moussy et al.

(10) Patent No.: US 9,078,894 B2
(45) Date of Patent: Jul. 14, 2015

(54) TREATMENT OF SEVERE PERSISTANT ASTHMA WITH MASITINIB

(75) Inventors: Alain Moussy, Paris (FR); Jean-Pierre Kinet, Lexington, MA (US)

(73) Assignee: AB SCIENCE, Paris (FR)

( * ) Notice: Subject to any disclaimer, the term of this patent is extended or adjusted under 35 U.S.C. 154(b) by 0 days.

(21) Appl. No.: 13/983,626

(22) PCT Filed: Feb. 3, 2012

(86) PCT No.: PCT/EP2012/051820
§ 371 (c)(1),
(2), (4) Date: Oct. 15, 2013

(87) PCT Pub. No.: WO2012/104402
PCT Pub. Date: Aug. 9, 2012

(65) Prior Publication Data
US 2014/0046063 A1     Feb. 13, 2014

Related U.S. Application Data

(60) Provisional application No. 61/439,549, filed on Feb. 4, 2011.

(51) Int. Cl.
| | |
|---|---|
| *A61K 31/426* | (2006.01) |
| *A61K 31/427* | (2006.01) |
| *A61K 31/496* | (2006.01) |
| *A61K 31/00* | (2006.01) |
| *A61K 45/06* | (2006.01) |

(52) U.S. Cl.
CPC .............. *A61K 31/496* (2013.01); *A61K 31/00* (2013.01); *A61K 45/06* (2013.01)

(58) Field of Classification Search
CPC .. A61K 31/426; A61K 31/427; A61K 31/496
USPC .................................................. 514/253.01
See application file for complete search history.

(56) References Cited

U.S. PATENT DOCUMENTS

2004/0115236 A1    6/2004   Chan et al.

FOREIGN PATENT DOCUMENTS

| WO | WO 2004/014903 | * | 2/2004 | .......... C07D 417/04 |
|---|---|---|---|---|
| WO | 2008/098949 | | 8/2008 | |

OTHER PUBLICATIONS

M. Humbert et al., "Masitinib, a . . . asthmatics", Allergy, vol. 64, No. 8, Aug. 1, 2009, pp. 1194-1201, XP55022568.
Rhee et al., "Effect of . . . chronic asthma", International Archives of Allergy and Immunology 2011, vol. 155, No. 3, Feb. 2, 2011, pp. 243-251, XP008150061.
Sano et al., "Effects of . . . refractory asthma", Respiratory Medicine, Bailliere Tindall, London, GB, vol. 100, No. 3, Mar. 1, 2006, pp. 420-433 XP005285312.
Karpel et al., "Effectiveness of . . . allergic asthma", Annals of Allergy, vol. 105, No. 6, Dec. 1, 2010, XP027544424.
N. Krishnamoorthy et al., "Activation of . . . allergic asthma", Nature Medicine 14, 565-573 (2008).
D.R. Taylor et al., "A new . . . and control", European Respiratory Journal, 2008, 32, 545-554.
L. Reber et al., "Stem cell . . . inflammatory diseases", European Journal of Pharmacology, 533, (2006) 327-340.
M. Humbert et al., "Benefits of . . . available therapy (GINA 2002 step 4 treatment: INNOVATE".
Ingram et al., "EGF and PDGF . . . lung diseases", PubMed, Curr Mol Med. Jun. 2006, 409-21.
Okayama et al., "Role of . . . airway remodeling", PubMed Curr Opin Immunol. Dec. 2007, 687-93, Epub Aug. 2007.
Kim et al., "Mast cells . . . model of asthma", PubMed Eur J. Immunol. Apr. 2007, 1107-15.
Gilfillan et al., "Integrated signaling . . . mast-cell activation", Nature Publishing Group, 2006, 218-230.
Dubreuil et al., "Masitinib, a Potent . . . Targeting Kit", Plos One, Sep. 2009, vol. 4, Issue 9.
Global Initiative for Asthma, Global Strategy for Asthma Management and Prevention, Updated 2007.
Global Initiative for Asthma, Global Strategy for Asthma Management and Prevention, Updated 2009.
Alasdair M. Gilfillan et al., "The tyrosine . . . mast cell activation", NIH Public Access, Immunol Rev. Mar. 2009; 228(1) 149-169.

* cited by examiner

Primary Examiner — Erich A Leeser
(74) Attorney, Agent, or Firm — Clark & Brody

(57) ABSTRACT

The present invention relates to the treatment of severe persistent asthma, and in particular severe persistent corticosteroid-dependent or corticosteroid-resistant asthma, comprising administration a tyrosine kinase inhibitor or a mast cell inhibitor, especially masitinib or a pharmaceutically acceptable salt thereof.

17 Claims, 4 Drawing Sheets

TREATMENT OF SEVERE PERSISTANT ASTHMA WITH MASITINIB

Figure 1:
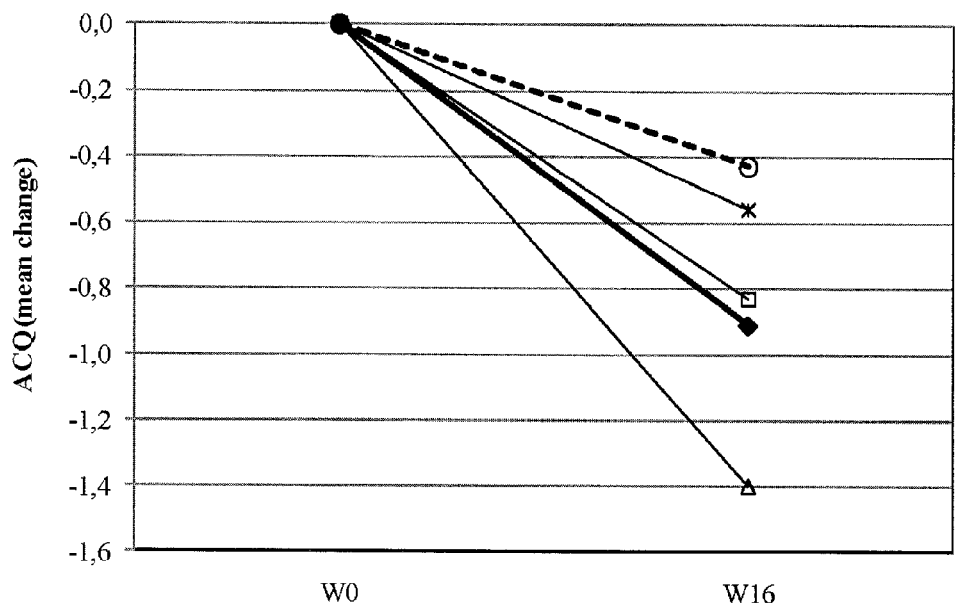

The present invention relates to the treatment of severe persistent asthma, and in particular severe persistent corticosteroid-dependent or corticosteroid-resistant asthma, comprising administration of a tyrosine kinase inhibitor or a mast cell inhibitor, especially masitinib or a pharmaceutically acceptable salt thereof.

BACKGROUND OF THE INVENTION

Asthma Overview

Asthma is a chronic inflammatory disorder of the airways in which many cells and cellular elements play a role. There is a growing consensus that airway inflammation is a critical element in the pathogenesis of asthma, and that asthma is in fact a chronic inflammatory syndrome in which inflammation promotes airway hyper-responsiveness and airway obstruction. This hyper-responsiveness leads to recurrent episode of wheezing, chest tightness, breathlessness and coughing particular at night or in the early morning. The recent success of anti-IgE therapies in asthma is supportive of this inflammatory mechanism. In addition to the inflammatory response, there are characteristic structural changes, often described as airway remodeling, in the airways of asthma patients. This remodeling process is related to disease severity, resulting in relatively irreversible narrowing of the airways. Such changes can be caused by inflammatory mediators, such as growth factors, and represent repair in response to chronic inflammation.

Asthma is a disease generally well controlled by inhaled treatments, bronchodilators and/or corticosteroids; however, between 5-10% of patients with asthma are relatively unresponsive to such standard treatments. Severe persistent asthma refers to patients whose symptoms remain difficult to control despite optimal management, treatment compliance, and extensive re-evaluation of diagnosis following an observation period of at least 6 months by an asthma specialist. These patients are considered either corticosteroid-dependent (normal pulmonary function maintained only if taking oral corticosteroid) or corticosteroid-resistant (poor pulmonary function despite treatment with oral corticosteroid). Such patients usually report recurrent symptoms, occurrence of exacerbations and a daily requirement of rescue medications. This lack of disease control generally has a strong negative impact on quality-of-life, compounded by the fact that oral corticosteroids can induce severe side effects, especially over the long-term. Although relatively uncommon, this refractory asthma population consumes a disproportionately large amount of health resource, and suffers from considerable morbidity and mortality.

The goal of asthma treatment is to achieve and maintain clinical control. Medications to treat asthma can be classified as controllers or relievers. Reliever medications act quickly to relieve bronchoconstriction and its accompanying acute symptoms. Controllers are medications taken daily on a long-terminal basis to keep asthma under clinical control, chiefly through their anti-inflammatory effects. Inhaled corticosteroids are currently the most effective anti-inflammatory medications for the treatment of persistent asthma. In patients that do not reach clinical control, add-on therapy with another class of controller is preferred over increasing the dose of inhaled corticosteroids. Long-term oral corticosteroid therapy (i.e., for periods longer than 2 weeks) may be required for severely uncontrolled asthma. However, patients on high-dose inhaled corticosteroids or oral corticosteroids at any dose are considered at risk of developing osteoporosis and fracture, but it is not certain whether this risk exists for patients on lower doses of inhaled corticosteroids.

Treatment options for severe persistent asthma patients, and in particular corticosteroid-refractory or corticosteroid-dependent severe persistent asthma, are limited and there is a large unmet clinical need for additional therapies. To date only omalizumab (Xolair®), an anti-immunoglobulin E antibody (anti-IgE), has European Medicines Agency approval for severe allergic asthma. Even so, a significant proportion of severe asthmatics are either not allergic or are not controlled by this therapy.

Diagnosis and Classification of Severe Persistent Asthma

There are various ways to classify asthma control; however, no classification is universally accepted. In general asthma can often be diagnosed on the basis of symptoms. However, measurements of lung function, and particularly the reversibility of lung function abnormalities, greatly enhance diagnostic confidence. A wide range of different methods to assess the level of airflow limitation exists, but two methods have found widespread acceptance for use in patients over 5 years of age. These are the measurement of forced expiratory volume in 1 second ($FEV_1$) and the measurement of peak expiratory flow (PEF). Both of these measurements depend on the concept of airflow limitation relating directly to the luminal size of the airways (airway caliber) and the elastic properties of the surrounding lung tissue (alveoli).

Asthma severity is conventionally classified by the presence of clinical features before treatment is started and/or by the amount of daily medication required for optimal treatment [Global Strategy for Asthma Management and Prevention, Global Initiative for Asthma (GINA) 2007; http://www.ginasthma.org]. Assessment of the level of airflow limitation and its variability enable asthma to be subdivided by severity into four steps: Intermittent, Mild Persistent, Moderate Persistent, and Severe Persistent (see Table 1). Thus, the severity of a patient's asthma may be classified into one of these four steps based on the clinical features present before treatment is begun. This type of asthma classification, based on severity, is important when decisions must be made about management at the initial assessment of a patient because asthma therapy involves a stepwise approach in which the level of therapy is increased as the severity of the asthma increases. It is important to recognize, however, that asthma severity involves both the severity of the underlying disease and its responsiveness to treatment [Global Strategy for Asthma Management and Prevention, Global Initiative for Asthma (GINA) 2009 update; http://www.ginasthma.org]. Thus, asthma could present with severe symptoms and airflow obstruction, but become completely controlled with low-dose treatment. In addition, severity is not a static feature of an individual patient's asthma, but may change over months or years. The main limitation of classification of asthma severity according to clinical features before treatment was its poor value in predicting what treatment would be required and what a patient's response to that treatment might be. For this reason, there is clinical utility in describing patients not only in relation to their level of asthma control, but also their asthma severity, in terms of the intensity of treatment required to treat the patient's asthma and to achieve good control.

TABLE 1

GINA Classification of Asthma Severity
by Clinical Features Before Treatment

Intermittent

Symptoms less than once a week
Brief exacerbations
Nocturnal symptoms not more than twice a month
$FEV_1$ or PEF ≥ 80% predicted
PEF or $FEV_1$ variability < 20%
Mild Persistent Symptoms more than once a week but less than once a day
Exacerbations may affect activity and sleep
Nocturnal symptoms more than twice a month
$FEV_1$ or PEF ≥ 80% predicted
PEF or $FEV_1$ variability < 20-30%
Moderate Persistent Symptoms daily
Exacerbations may affect activity and sleep
Nocturnal symptoms more than once a week
Daily use of inhaled short-acting $β_2$-agonist
$FEV_1$ or PEF 60-80% predicted
PEF or $FEV_1$ variability > 30%
Severe Persistent Symptoms daily
Frequent exacerbations
Frequent nocturnal asthma symptoms
Limitation of physical activities
$FEV_1$ or PEF ≤ 60% predicted
PEF or $FEV_1$ variability > 30%

*The worst feature determines the severity classification.
Taken from Global Strategy for Asthma Management and Prevention, Global Initiative for Asthma (GINA) 2007; http://www.ginasthma.org In view of these limitations, asthma severity is now by consensus classified on the basis of the intensity of treatment required to achieve good asthma control [Taylor et al., Eur Respir J. 2008 September; 32(3):545-54]. Mild asthma is asthma that can be well-controlled with low intensity treatment such as low-dose controller medications such as inhaled corticosteroids, Severe asthma is asthma that requires high intensity treatment by controller medications, for example oral corticosteroids, to maintain good control, or where good control is not achieved despite high intensity treatment. Thus, initial assessment of severity (and hence the starting treatment step) can be decided off-treatment using the GINA classification of asthma severity according to clinical features; however, once the patient is on treatment, the classification of severity should be based on the clinical features present and the step of the daily medication regimen that the patient is currently on (Table 2). In this model, worsening severity was defined by worsening clinical control and/or increasing treatment requirements, i.e. by any movement to the right or downwards in the table.

TABLE 2

GINA Classification of Asthma Severity by Daily Medication
Regimen and Response to Treatment. [Global Strategy
for Asthma Management and Prevention, Global Initiative
for Asthma (GINA) 2005; http://www.ginasthma.org]

| | Current treatment step | | |
|---|---|---|---|
| Patient symptoms and lung function | Step 1: intermittent | Step 2: mild persistent | Step 3: moderate persistent |
| Step 1: intermittent | Intermittent | Mild persistent | Moderate persistent |
| Symptoms less than once per week Brief exacerbations Nocturnal symptoms not more than twice per month Normal lung function between episodes | | | |
| Step 2: mild persistent Symptoms more than once per week but less than once per day Nocturnal symptoms more than twice per month but less than once per week Normal lung function between episodes | Mild persistent | Moderate persistent | Severe persistent |
| Step 3: moderate persistent Symptoms daily Exacerbations may affect activity and sleep Nocturnal symptoms at least once per week FEV1 >60 and <80% pred or PEF >60 and <80% of personal best | Moderate persistent | Severe persistent | Severe persistent |
| Step 4: severe persistent Symptoms daily Frequent exacerbations Frequent nocturnal asthma symptoms FEV1 ≤60% pred or PEF ≤60% of personal best | Severe persistent | Severe persistent | Severe persistent |

The patient's severity classification was increased (worsened) by one step for each increased step in treatment. Any change towards the right or towards the bottom of the table represented worsening severity. Treatments are as defined in [7]. FEV1: forced expiratory volume; % pred: % predicted; PEF: peak expiratory flow
Table taken from Taylor et al., Eur Respir J. 2008 September; 32(3): 545-54.

Treatment of Severe Persistent Asthma

The main controller medications used in severe asthma include high-dose inhaled corticosteroids, oral corticosteroids, and anti-IgEs. Other controller medications, sometimes referred to as steroid-sparing therapies because they have an advantage of reducing the corticosteroid intake, could be given to severe asthma patients as an add-on therapy; examples include, leukotriene modifiers, long-acting inhaled β-agonists, and sustained-release theophylline.

Inhaled corticosteroids are currently the most effective anti-inflammatory medications for the treatment of persistent asthma. Studies have demonstrated their efficacy in reducing asthma symptoms, improving quality-of-life, improving lung function, decreasing airway hyper-responsiveness, controlling airway inflammation, reducing frequency and severity of exacerbations, and reducing asthma mortality. However, they do not cure asthma and when discontinued a deterioration of clinical control follows within weeks to months in a proportion of patients. To reach clinical control, add-on therapy with another class of controller is preferred over increasing the dose of inhaled corticosteroids. There is, however, a clear relationship between the dose of inhaled corticosteroids and the prevention of severe acute exacerbations of asthma. Therefore, some patients with severe asthma may benefit from long-term treatment with higher doses of inhaled corticosteroids. Local adverse effects from inhaled corticosteroids include oropharyngeal candidiasis, dysphonia, and occasionally coughing from upper airway irritation.

Leukotriene modifiers include cysteinyl leukotriene 1 (CysLT1) receptor antagonists (montelukast, pranlukast, and zafirlukast) and a 5-lipoxygenase inhibitor (zileuton). Clinical studies have demonstrated that leukotriene modifiers have a small and variable bronchodilator effect, reduce symptoms including cough, improve lung function, and reduce airway inflammation and asthma exacerbations. Leukotriene modifiers used as add-on therapy may reduce the dose of inhaled corticosteroids required by patients with moderate to severe asthma, and may improve asthma control in patients whose asthma is not controlled with low or high doses of inhaled corticosteroids. Leukotriene modifiers are well tolerated, and few if any class-related effects have so far been recognized. Zileuton has been associated with liver toxicity, and monitoring of liver tests is recommended during treatment with this medication.

Long-acting inhaled β2-agonists, including formoterol and salmeterol, should not be used as monotherapy in asthma as these medications do not appear to influence the airway inflammation in asthma. They are most effective when combined with inhaled corticosteroids, and this combination therapy is the preferred treatment when a medium dose of inhaled corticosteroid alone fails to achieve control of asthma. Addition of long-acting inhaled β2-agonists to a daily regimen of inhaled corticosteroids improves symptom scores, decreases nocturnal asthma. Therapy with long-acting inhaled β2-agonists causes fewer systemic adverse effects—such as cardiovascular stimulation, skeletal muscle tremor, and hypokalemia—than oral therapy. Data indicating a possible increased risk of asthma-related death associated with the use of salmeterol in a small group of individuals led to advisories from the US Food and Drug Administration (FDA) and Health Canada that long-acting β2-agonists are not a substitute for inhaled or oral corticosteroids, and should only be used in combination with an appropriate dose of inhaled corticosteroid as determined by a physician.

Theophylline is a bronchodilator and, when given in a lower dose, has modest anti-inflammatory properties. Available evidence suggests that sustained-release theophylline has little effect as a first-line controller. It may provide benefit as add-on therapy in patients who do not achieve control on inhaled corticosteroids alone. Sides effects of theophylline, particularly at higher doses (10 mg/kg body weight/day or more), are significant and reduce their usefulness. Adverse effects include gastrointestinal symptoms, loose stools, cardiac arrhythmias, seizures, and even death. Nausea and vomiting are the most common early events.

Anti-IgE (omalizumab, Xolair®) is a treatment option limited to patients with elevated serum levels of IgE. Its current indication is for patients with severe allergic asthma who are uncontrolled on inhaled corticosteroids, although the dose of concurrent treatment has varied in different studies. Improved asthma control is reflected by fewer symptoms, less need for reliever medications, and fewer exacerbations. As indicated by several studies involving asthma patients between the ages of 11 and 50, who were already receiving treatment with corticosteroids (inhaled and/or oral) and longacting β2-agonists, anti-IgE appears to be safe as add-on therapy. However, anaphylaxis has been reported to occur after administration of omalizumab in premarketing clinical trials and in postmarketing spontaneous reports. In postmarketing spontaneous reports, the frequency of anaphylaxis attributed to omalizumab use was estimated to be at least 0.2% of patients based on an estimated exposure of about 57,300 patients from June 2003 through December 2006. Anaphylaxis has occurred as early as after the first dose of omalizumab, but also has occurred beyond 1 year after beginning regularly scheduled treatment. Additionally, malignant neoplasms were observed in 20 of 4127 (0.5%) omalizumab-treated patients compared with 5 of 2236 (0.2%) control patients in clinical studies of asthma and other allergic disorders.

Long-term oral corticosteroid therapy (that is, for periods longer than 2 weeks as a corticosteroid "burst") may be required for severely uncontrolled asthma, but its use is limited by the risk of significant adverse effects. The therapeutic index (effect/side effect) of long-teen inhaled corticosteroids is always more favorable than long-term oral corticosteroids in asthma. The systemic side effects of long-term oral or parenteral corticosteroid treatment include osteoporosis, arterial hypertension, diabetes, hypothalamicpituitary-adrenal axis suppression, obesity, cataracts, glaucoma, skin thinning leading to cutaneous striae and easy bruising, and muscle weakness. Patients with asthma who are on long-term oral corticosteroids in any form should receive preventive treatment for osteoporosis. Although it is rare, withdrawal of oral corticosteroids can elicit adrenal failure or unmask underlying disease, such as Churg-Strauss Syndrome.

Various therapeutic regimens to reduce the dose of oral corticosteroids required by patients with severe asthma have been proposed, including methotrexate, cyclosporin and gold. These medications should be used only in selected patients under the supervision of an asthma specialist, as their potential steroid-sparing effects may not outweigh the risk of serious side effects. Two meta-analyses of the steroid sparing effect of low-dose methotrexate showed a small overall benefit, but a relatively high frequency of adverse effects. Methotrexate may cause gastrointestinal symptoms, and on rare occasions hepatic and diffuse pulmonary parenchymal disease, and hematological and teratogenic effects. The modest potential to reduce the impact of corticosteroid side effects is probably insufficient to offset the adverse effects of methotrexate.

Despite these treatment options the unmet medical need in severe persistent asthma remains substantial, in particular for corticosteroid-refractory or corticosteroid-dependent severe persistent asthma. Several reasons can be given for this:

None of the available drugs cure or completely stop the disease process and in certain refractory populations are not particularly effective in controlling the disease.

The recently approved anti-IgE treatment (omalizumab, Xolair®) is administered via subcutaneous injection once every 2 or 4 weeks and due to a risk of anaphylaxis it must be administered by a patients health care provider. Considering the chronic nature of this disease, this method of delivery is likely to impact negatively on the patient's adherence to treatment, quality-of-life and can lead to a common side effect of injection site reactions.

Long-term treatment regimens using corticosteroids are associated with numerous detrimental side effects, with its benefits possibly outweighed by potential complications. Important adverse events in clinical trials are reported for existing treatments.

Conventional treatments for severe asthma, including corticosteroid and long-acting inhaled β2-agonists, may become inefficient for controlling disease activity and progression in severe persistent asthma.

Thus, beyond the already developed therapeutic strategies, there exists an imperative need to identify alternative treatments for severe asthma that demonstrate high efficacy over time in monotherapy, allow for reduction of oral and/or inhaled corticosteroid dose, i.e. steroid-sparing or weaning, exploit novel therapeutic targets for more effective combination therapies, minimize toxicity and are affordable. One such approach involves blocking intracellular proinflammatory messages, which is currently represented by the strategy of selective protein tyrosine kinase inhibition.

Role of c-Kit and Mast Cells in Inflammation

Mast cells are predominantly found in tissues at the interface between the host and the external environment, such as lung, connective tissue, lymphoid tissue, gut mucosa, and skin. Immature mast cells progenitors circulate in the bloodstream and differentiate in tissues. These differentiation and proliferation processes are influenced by cytokines, notably Stem Cell Factor (SCF). The SCF receptor is encoded by the proto-oncogene c-Kit. It has been shown that SCF regulates the migration, maturation, proliferation, and activation of mast cells in vivo—injection of recombinant SCF into rodents, primates, or humans, results in an increase in mast cell numbers at both the site of injection and at distant sites.

Mast cells are characterized by their heterogeneity, not only regarding tissue location and structure but also at functional and histochemical levels. Mast cell activation is followed by the controlled release of a variety of mediators that are essential for the defense of the organism against invading pathogens. By contrast, in the case of hyperactivation of mast cells, uncontrolled hypersecretion of these mediators is deleterious for the body. Mast cells produce a large variety of mediators categorized here into three groups:

Preformed granule-associated mediators (histamines, proteoglycans, and neutral proteases);

Lipid-derived mediators (prostaglandins, thromboxanes and leucotrienes);

Various cytokines (including the interleukins IL-1, IL-2, IL-3, IL-4, IL-5, IL-6, IL-8 and tumor necrosis factor alpha TNF-α, GM-CSF, MIP-1α, MIP-1β and IFN-γ).

Human mast cells constitutively express a number of receptors for different biological molecules. Among these receptors, whose ligation induces the activation of mast cells, the best known is the high affinity receptor for IgE (FcεRI). Binding of IgE-multivalent antigen complexes to FcεRI leads to receptor aggregation and internalization, signaling, and degranulation. This can be accompanied by the transcription of cytokine genes, thus, perpetuating the inflammatory response. Moreover, triggering of mast cells leads to the secretion of diverse pre-formed and/or de novo synthesized mediators, such as vasoactive amines (histamine, serotonin), sulfated proteoglycans, lipid mediators (prostaglandin D2, leucotrienes), growth factors, proteases, cytokines and chemokines as described previously. These mediators can, alone or in synergy with macrophage-derived and T cell-derived cytokines, generate a complex inflammatory response and induce the recruitment and activation of inflammatory cells to the site of degranulation.

AIMS OF THE INVENTION

The invention aims to solve the technical problem of providing an active ingredient for the treatment of severe persistent asthma, and in particular for severe persistent corticosteroid-dependent or corticosteroid-resistant asthma.

The invention aims to provide an efficient treatment for such a disease at an appropriate dose, route of administration and daily intake.

The invention also aims to solve the technical problem of providing an active ingredient that improves prior art methods for the treatment of severe asthma.

The invention also aims to solve the technical problem of providing an active ingredient that promotes a steroid-saving effect; that is, it permits a reduction in a patient's intake of inhaled corticosteroids and/or of long-term oral corticosteroid therapy.

SUMMARY OF THE INVENTION

The invention relates to a tyrosine kinase inhibitor or a mast cell inhibitor, especially masitinib or a pharmaceutically acceptable salt thereof, for the treatment of severe persistent asthma, and in particular severe persistent corticosteroid-dependent or corticosteroid-resistant asthma, in human patients, wherein said tyrosine kinase inhibitor or mast cell inhibitor is to be administered to patients in need thereof, optionally combined with at least one corticosteroid or other controller medication.

The invention also relates to a method of treatment of severe persistent asthma, and in particular severe persistent corticosteroid-dependent or corticosteroid-resistant asthma, wherein a tyrosine kinase inhibitor or a mast cell inhibitor, especially masitinib or a pharmaceutically acceptable salt thereof, is to be administered in patients in need thereof, optionally combined with at least one corticosteroid or other controller medication.

In one embodiment, the invention relates to a method of treatment of severe persistent asthma, in particular severe persistent corticosteroid-dependent or corticosteroid-resistant asthma, wherein a tyrosine kinase inhibitor or a mast cell inhibitor, especially masitinib or a pharmaceutically acceptable salt thereof, is an inhibitor of c-Kit, Lyn, Fyn and PDGFR kinase activity.

In another embodiment, the invention also relates to a method of treatment of severe persistent asthma, in particular severe persistent corticosteroid-dependent or corticosteroid-resistant asthma, wherein a tyrosine kinase inhibitor or a mast cell inhibitor, especially masitinib or a pharmaceutically acceptable salt thereof, is administered for the treatment of severe persistent asthma in combination with at least one other asthma controller medication; for example, inhaled and systemic corticosteroids, leukotriene modifiers, long-acting inhaled β2-agonists, sustained-release theophylline, cromones, anti-IgE, and other systemic steroid-sparing therapies.

In yet another embodiment, the invention also relates to a method of treatment of severe persistent asthma, in particular severe persistent corticosteroid-dependent or corticosteroid-resistant asthma, wherein a tyrosine kinase inhibitor or a mast cell inhibitor, especially masitinib or a pharmaceutically acceptable salt thereof, acts as a systemic steroid-sparing therapy.

DESCRIPTION OF THE INVENTION

Role of c-Kit and Mast Cells in Asthma

A classical view of the pathogenesis of the asthmatic inflammation is that following the immunization phase and the development of an immune response, allergens initiate the inflammatory process by triggering IgE-bearing pulmonary mast cells. Mast cells are well known for their involvement in allergic and anaphylactic reactions. Recent findings implicate them in a variety of inflammatory diseases affecting different organs, including the heart, joints, lungs, and skin. In some cases mast cells appear to be activated by triggers other than aggregation of their IgE receptors, leading to selective release of mediators without degranulation. Once activated mast cells release multiple mediators that produce a localized allergic response, and subsequently, secrete various cytokines, which then participate in the local recruitment and activation of other inflammatory cells such as eosinophils, basophils, T lymphocytes and mononuclear phagocytes. These recruited cells, in turn, contribute to the development of an inflammatory response, which may then become persistent, and thereby perpetuate the reaction. These events explain some of the symptoms found in immune-mediated diseases such as asthma.

Mast cells and dendritic cells are likely to play a major role in severe asthma. It is known that activated mast cells release bronchoconstrictor mediators such as histamine, cysteinyl leukotrines, prostaglandine D2, moreover, mast cells were found to contribute to the development of multiple features of chronic asthma in mast cell deficient mice (Okayama Y et al. Curr Opin Immunol. 2007 19(6):687-93). Experimental data has also indicated that dendritic cells expressing non-functional c-Kit elicited diminished allergic airway inflammation [Krishnammorty N, et al. Nat Med 2008]. These cells can be activated through the engagement of the stem cell factor (SCF) receptor c-Kit and therefore, inhibition of the SCF/c-Kit pathway may be a potential therapeutic target. For example, SCF the ligand of the c-Kit receptor, is a major growth factor for mast cell survival, proliferation, differentiation, adhesion and degranulation processes (Reber et al., Eur J Pharmacol 2006; 533:327-340), with SCF-dependent activation of c-Kit critical for mast cell homeostasis and function. It is thought that inhibition of c-Kit would therefore lead to a decrease in mast cell population, histamine levels, eosinophile infiltration, interleukin-4 production and airway hyper-responsiveness.

Beyond the role mast cells play in immediate hypersensitivity and late phase inflammation, an increased abundance of mast cells in the airways of asthmatics also implicates mast cells to the earlier phase of airway tissue remodeling (Okayama Y et al. Curr Opin Immunol. 2007 19(6):687-93). Increased Airway Smooth Muscle (ASM) mass is recognized as one of the most important factors related to persistent airway hyper-responsiveness (AHR) and to the severity of asthma. The infiltration of ASM by mast cells is associated with the disordered airway function, with mediators such as tryptase and cytokines from mast cells capable of modulating ASM cell function to induce goblet cell hyperplasia. Additionally, mast cells are associated with the development of late AHR through liberation of TNF-alpha (Kim Y S et al. Eur J Immunol. 2007 37(4):1107-15).

Role of Platelet-Derived Growth Factor Receptor in Asthma

Aberrant expression or signaling patterns of the platelet-derived growth factor receptor (PDGFR) family of receptor tyrosine kinases has also been linked to the progression of a diversity of diseases and has been shown to contribute to bronchial remodeling, characteristic of severe asthma [Ingram J L, et al. Curr Mol Med 2006]. Targeting PDGF receptor tyrosine kinase may be an interesting novel therapeutic option for severe asthma patients.

Tyrosine Kinase Inhibitors (Compounds of the Invention)

Tyrosine kinases are receptor type or non-receptor type proteins, which transfer the terminal phosphate of ATP to tyrosine residues of proteins thereby activating or inactivating signal transduction pathways. These proteins are known to be involved in many cellular mechanisms, which in case of disruption, lead to disorders such as abnormal cell proliferation and migration as well as inflammation. A tyrosine kinase inhibitor is a drug that inhibits tyrosine kinases, thereby interfering with signaling processes within cells. Blocking such processes can stop the cell growing and dividing.

Such Tyrosine Kinase Inhibitors are an optionally substituted 2-(3-aminoaryl)amino-4-aryl-thiazoles is preferably of the following formula I.

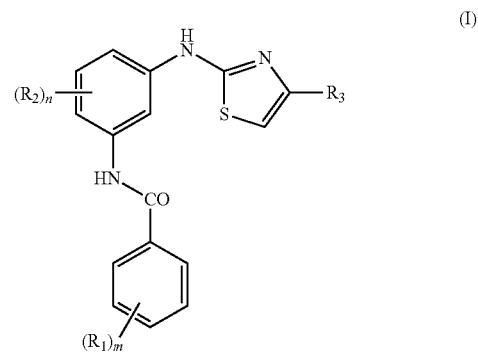

Wherein:

R1 and R2 are selected independently from hydrogen, halogen, a linear or branched alkyl, cycloalkyl group containing from 1 to 10 carbon atoms, trifluoromethyl, alkoxy, cyano, amino, alkylamino, dialkylamino, solubilizing group.

m is 0-5 and n is 0-4.

R3 is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, cyano and alkoxy;

(ii) a heteroaryl group such as 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.

Unless otherwise specified, the below terms used herein are defined as follows:

As used herein, the term an "aryl group" means a monocyclic or polycyclic-aromatic radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents.

In one embodiment, the aryl group is a monocyclic ring, wherein the ring comprises 6 carbon atoms, referred to herein as "(C6)aryl."

As used herein, the term "alkyl group" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents.

As used herein, the term "alkoxy" refers to an alkyl group which is attached to another moiety by an oxygen atom. Examples of alkoxy groups include methoxy, isopropoxy, ethoxy, tert-butoxy, and the like. Alkoxy groups may be optionally substituted with one or more substituents.

As used herein, the term "heteroaryl" or like terms means a monocyclic or polycyclic heteroaromatic ring comprising carbon atom ring members and one or more heteroatom ring members (such as, for example, oxygen, sulfur or nitrogen). Typically, a heteroaryl group has from 1 to about 5 heteroatom ring members and from 1 to about 14 carbon atom ring members. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzo(b)thienyl. A heteroatom may be substituted with a protecting group known to those of ordinary skill in the art, for example, the hydrogen on a nitrogen may be substituted with a tert-butoxycarbonyl group. Heteroaryl groups may be optionally substituted with one or more substituents. In addition, nitrogen or sulfur heteroatom ring members may be oxidized. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings.

The term "heterocycle" as used herein, refers collectively to heterocycloalkyl groups and heteroaryl groups.

As used herein, the term "heterocycloalkyl" means a monocyclic or polycyclic group having at least one heteroatom selected from O, N or S, and which has 2-11 carbon atoms, which may be saturated or unsaturated, but is not aromatic. Examples of heterocycloalkyl groups including (but not limited to): piperidinyl, piperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyridinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 members. Preferred 3 to 7 membered monocyclic heterocycloalkyl groups are those having 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be optionally substituted with one or more substituents. In addition, the point of attachment of a heterocyclic ring to another group may be at either a carbon atom or a heteroatom of a heterocyclic ring. Only stable isomers of such substituted heterocyclic groups are contemplated in this definition.

As used herein the term "substituent" or "substituted" means that a hydrogen radical on a compound or group is replaced with any desired group that is substantially stable to reaction conditions in an unprotected form or when protected using a protecting group. Examples of preferred substituents are those found in the exemplary compounds and embodiments disclosed herein, as well as halogen (chloro, iodo, bromo, or fluoro); alkyl; alkenyl; alkynyl; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (—O); haloalkyl (e.g., trifluoromethyl); cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl), monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); $CO_2CH_3$; $CONH_2$; $OCH_2CONH_2$; $NH_2$; $SO_2NH_2$; $OCHF_2$; $CF_3$; $OCF_3$; and such moieties may also be optionally substituted by a fused-ring structure or bridge, for example —$OCH_2O$—. These substituents may optionally be further substituted with a substituent selected from such groups. In certain embodiments, the term "substituent" or the adjective "substituted" refers to a substituent selected from the group consisting of an alkyl, an alkenyl, an alkynyl, an cycloalkyl, an cycloalkenyl, a heterocycloalkyl, an aryl, a heteroaryl, an aralkyl, a heteraralkyl, a haloalkyl, —C(O)NR11R12, —NR13C(O)R14, a halo, —OR13, cyano, nitro, a haloalkoxy, —C(O)R13, —NR11R12, —SR13, —C(O)OR13, —OC(O)R13, —NR13C(O)NR11R12, —OC(O)NR11R12, —NR13C(O)OR14, —S(O)rR13, —NR13S(O)rR14, —OS(O)rR14, S(O)rNR11R12, —O, —S, and —N—R13, wherein r is 1 or 2; R11 and R12, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; or R1 and R12 taken together with the nitrogen to which they are attached is optionally substituted heterocycloalkyl or optionally substituted heteroaryl; and R13 and R14 for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl. In certain embodiments, the term "substituent" or the adjective "substituted" refers to a solubilizing group.

The term "solubilizing group" means any group which can be substantially ionized and that enables the compound to be soluble in a desired solvent, such as, for example, water or water-containing solvent. Furthermore, the solubilizing group can be one that increases the compound or complex's lipophilicity. Typically, the solubilizing group is selected from alkyl group substituted with one or more heteroatoms such as N, O, S, each optionally substituted with alkyl group substituted independently with alkoxy, amino, alkylamino, dialkylamino, carboxyl, cyano, or substituted with cycloheteroalkyl or heteroaryl, or a phosphate, or a sulfate, or a carboxylic acid.

For example, by "solubilizing group" it is referred herein to one of the following:

- an alkyl, cycloalkyl, aryl, heretoaryl group comprising either at least one nitrogen or oxygen heteroatom or which group is substituted by at least one amino group or oxo group.
- an amino group which may be a saturated cyclic amino group which may be substituted by a group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl.
- one of the structures a) to i) shown below, wherein the wavy line and the arrow line correspond to the point of attachment to core structure of formula I.

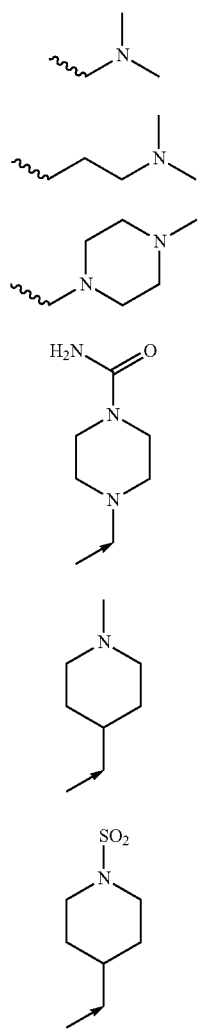

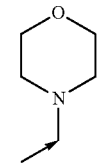

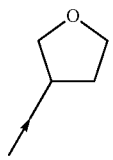

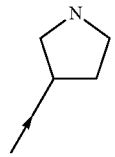

The term "cycloalkyl" means a saturated cyclic alkyl radical having from 3 to 10 carbon atoms. Representative cycloalkyls include cyclopropyl, 1-methylcyclopropyl, cyclobutyl, cyclopentyl, cyclohexyl, cycloheptyl, cyclooctyl, cyclononyl, and cyclodecyl. Cycloalkyl groups can be optionally substituted with one or more substituents.

The term "halogen" means —F, —Cl, —Br or —I.

In a particular embodiment the invention relates to a compound of formula II, or a pharmaceutical acceptable salt thereof,

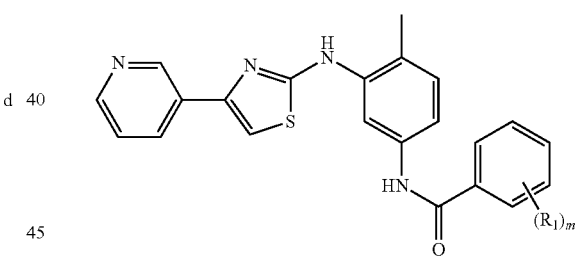

(II)

Wherein:

R1 is selected independently from hydrogen, halogen, a linear or branched alkyl, cycloalkyl group containing from 1 to 10 carbon atoms, trifluoromethyl, alkoxy, amino, alkylamino, dialkylamino, solubilizing group.

m is 0-5.

Masitinib is an Inhibitor of c-Kit and PDGFR with a Potent Anti Mast Cell Action We discovered in this regard, new potent and selective c-Kit inhibitors which are 2-(3-aminoaryl)amino-4-aryl-thiazoles described in AB Science's PCT application WO 2004/014903.

Masitinib is a small molecule selectively inhibiting specific tyrosine kinases such as c-Kit, PDGFR, Lyn, Fyn and to a lesser extent the fibroblast growth factor receptor 3 (FGFR3), without inhibiting, at therapeutic doses, kinases associated with known toxicities (i.e. those tyrosine kinases or tyrosine kinase receptors attributed to possible tyrosine kinase inhibitor cardiac toxicity, including ABL, KDR and Src) (Dubreuil et al., 2009, PLoS ONE 2009.4(9):e7258). The chemical name for masitinib is 4-(4-methylpiperazin-1-ylmethyl)-N-[4-methyl-3-(4-pyridin-3ylthiazol-2-ylamino)phenyl]benzamide—CAS number 790299-79-5, and the structure is shown below. Masitinib was first described in U.S. Pat. No. 7,423,055 and EP1525200B1. A detailed procedure for the synthesis of masitinib mesilate is given in WO2008/098949.

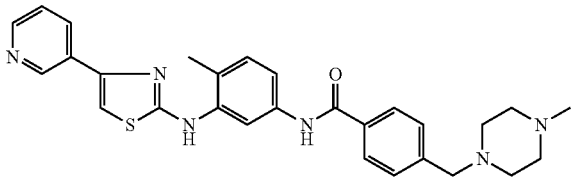 [SMILES: Cc1ccc(NC(=O)c2ccc(CN3CCN(C)CC3)cc2)cc1Nc1nc(-c2cccnc2)cs1]

Masitinib's strong inhibitory effect on wild-type and juxtamembrane-mutated c-Kit receptors, results in cell cycle arrest and apoptosis of cell lines dependent on c-Kit signaling (Dubreuil et al., 2009, PLoS ONE, 4(9):e7258). Stem cell factor, the ligand of the c-Kit receptor, is a critical growth factor for mast cells; thus, masitinib is an effective antimastocyte, exerting a direct antiproliferative and pro-apoptotic action on mast cells through its inhibition of c-Kit signaling. In vitro, masitinib demonstrated high activity and selectivity against c-Kit, inhibiting recombinant human wild-type c-Kit with an half inhibitory concentration ($IC_{50}$) of 200±40 nM and blocking stem cell factor-induced proliferation and c-Kit tyrosine phosphorylation with an $IC_{50}$ of 150±80 nM in Ba/F3 cells expressing human or mouse wild-type c-Kit.

In addition to its antiproliferative properties, masitinib can also regulate the activation of mast cells through its targeting of Lyn and Fyn, key components of the transduction pathway leading to IgE induced degranulation (Gilfillan & Tkaczyk, 2006, Nat Rev Immunol, 6:218-230; Gilfillan et al., 2009, Immunological Reviews, 228:149-169). This can be observed in the inhibition of FcεRI-mediated degranulation of human cord blood mast cells (Dubreuil et al., 2009, PLoS ONE; 4(9):e7258).

Masitinib is also a potent inhibitor of PDGFR α and β receptors. Recombinant assays show that masitinib inhibits the in vitro protein kinase activity of PDGFR-α and β with $IC_{50}$ values of 540±60 nM and 800±120 nM. In Ba/F3 cells expressing PDGFR-α, masitinib inhibited PDGF-BB-stimulated proliferation and PDGFR-α tyrosine phosphorylation (FIG. 5B) with an $IC_{50}$ of 300±5 nM.

Dose response analyses from clinical trials of masitinib in the treatment of non-oncological indications relevant to severe asthma, that is to say, inflammatory diseases or autoimmune diseases with mast cell involvement such as rheumatoid arthritis and indolent forms of mastocytosis, have shown that a masitinib dose level of 6 mg/kg/day is the optimal starting dose with respect to potency and tolerability; providing an acceptable balance between therapeutic benefit and risk.

Treatment of Severe Persistent Asthma with Masitinib

Molecules able to inhibit the survival and/or activation of mast cells may be able to control the symptoms and progression of severe persistent asthma. In connection with the invention, we consider that a tyrosine kinase inhibitor or a mast cell inhibitor, notably as defined above, especially masitinib, through its inhibition of mast cell proliferation and activation, is fulfilling this role in the treatment of severe persistent asthma via, but not limited to, reducing the overall mast cell burden and inhibiting the global activity of mast cells.

Molecules able to inhibit the processes of airway remodeling may be able to control the symptoms and progression of severe persistent asthma. In connection with the invention, we consider that a tyrosine kinase inhibitor or a mast cell inhibitor, notably as defined above, especially masitinib, through its inhibition of PDGFR and anti mast cell activity, is fulfilling this role in the treatment of severe persistent asthma via, but not limited to, reducing the infiltration of airway smooth muscle by mast cells and regulating the activity of PDGFR in airway smooth muscle cell growth.

Thus, in a first embodiment, the invention relates to the use of at least one compound of the invention (i.e. a tyrosine kinase inhibitor or a mast cell inhibitor, especially masitinib or a pharmaceutically acceptable salt thereof), for the preparation of a medicament for the treatment of severe persistent asthma, and in particular severe persistent corticosteroid-dependent or corticosteroid-resistant asthma, in human patients, wherein said a tyrosine kinase inhibitor or a mast cell inhibitor is to be administered to patients in need thereof, optionally combined with at least one corticosteroid or other controller medication, and wherein said patients optionally suffer from GINA-defined severe persistent asthma in accordance to the classification of asthma severity by daily medication regimen and response to treatment, or have a $FEV_1 \leq 60\%$ predicted or $PEF \leq 60\%$ of personal best.

The invention thus relates to a method of treatment of severe persistent asthma, and in particular severe persistent corticosteroid-dependent or corticosteroid-resistant asthma, in human patients, wherein at least one compound of the invention is to be administered in patients in need thereof, optionally combined with at least one corticosteroid or other controller medication, and wherein said patients suffer from suffer from GINA-defined severe persistent asthma in accordance to the classification of asthma severity by daily medication regimen and response to treatment, or have a $FEV_1 \leq 60\%$ predicted or $PEF \leq 60\%$ of personal best.

Preferably, said patients are those afflicted by severe persistent asthma; more specifically with $FEV_1 \leq 60\%$ predicted or $PEF \leq 60\%$ of personal best, or GINA-defined severe persistent asthma in accordance to the classification of asthma severity by daily medication regimen and response to treatment.

According to another embodiment, said compound of the invention is to be administered for the treatment of severe persistent corticosteroid-resistant asthma.

According to an embodiment, said compound of the invention is to be administered for the treatment of severe persistent corticosteroid-dependent asthma.

Advantageously, for patients afflicted with severe persistent corticosteroid-dependent asthma, zthe use or method comprises the administration of an effective amount of said tyrosine kinase inhibitor or mast cell inhibitor, especially masitinib or a pharmaceutically acceptable salt thereof, permits a reduction in a patient's intake of inhaled corticosteroids and/or of long-term oral corticosteroid therapy; that is to say, it promotes a steroid-saving effect.

According to one embodiment, the schedule for corticosteroid reduction or weaning is as follows: oral corticosteroid dose will be decreased by, for example, 25% every week until a worsening of asthma occurs. As soon as a patient experiences a worsening of asthma, corticosteroid should be reintroduced at the dose of the previous week.

According to one embodiment, a compound of the invention is an inhibitor of c-Kit, PDGFR, Lyn and Fyn kinase activity.

According to another embodiment, a compound of the invention is to be administered at a starting daily dose of 3.0 to 6.0 mg/kg/day±1.5 mg/kg/day, with the preferred embodiment for patients with severe persistent asthma being a starting daily dose of 4.5 to 6.0 mg/kg/day.

Preferably, a compound of the invention is dose escalated by increments of 1.5 mg/kg/day to reach a maximum of 9.0 mg/kg/day, notably in low responder patients.

Said compound of the invention is preferably administered orally.

Said compound of the invention is preferably administered twice a day.

Indeed, depending on age, individual condition, mode of administration, and the clinical setting, effective doses of said tyrosine kinase inhibitor or mast cell inhibitor, especially masitinib or a pharmaceutically acceptable salt thereof, in human patients with severe persistent asthma are 3.0 to 6.0 mg/kg/day per os, preferably in two daily intakes. For adult human patients with severe persistent asthma, a starting dose of said tyrosine kinase inhibitor or mast cell inhibitor, especially masitinib or a pharmaceutically acceptable salt thereof, of 4.5 to 6.0 mg/kg/day has been found to be the preferred embodiment according to the invention. For patients with an inadequate response after an assessment of response to therapy and in the absence of limiting toxicities, dose escalation of said tyrosine kinase inhibitor or mast cell inhibitor, especially masitinib or a pharmaceutically acceptable salt thereof, to a maximum of 9.0 mg/kg/day can be safely considered and patients may be treated as long as they benefit from treatment and in the absence of limiting toxicities.

Dose adjustment can be considered a dynamic process, with a patient undergoing multiple increases and/or decreases to optimize the balance between response and toxicity throughout treatment, both of which are likely to vary over time and duration of drug exposure. If dose escalation is undertaken, it is suggested that the starting dose of 3.0 to 6.0±1.5 mg/kg/day be incremented by 1 to 2 mg/kg/day up to a maximum dose of 9.0 mg/kg/day, over a period which depends upon clinical observations. For example, a single dose escalation of said tyrosine kinase inhibitor or mast cell inhibitor, especially masitinib or a pharmaceutically acceptable salt thereof, and preferably masitinib mesilate may take from 1 to 2 months. It is also contemplated herein that to fully obtain the therapeutic benefits of a patient-optimized dose of said tyrosine kinase inhibitor or mast cell inhibitor, especially masitinib or a pharmaceutically acceptable salt thereof, dose increments smaller than 1 to 2 mg/kg/day could be implemented. Dose reduction is to be considered to reduce toxicity in appropriate cases.

Any dose indicated herein refers to the amount of active ingredient as such, not to its salt form.

Advantageously, the use or method comprises a long-term administration of an effective amount of said tyrosine kinase inhibitor or mast cell inhibitor, especially masitinib or a pharmaceutically acceptable salt thereof, over more than 3 months, preferably more than 12 months.

For example, said pharmaceutical composition comprises a dose of at least 50 mg and less than 150 mg, and preferably of 100 mg, of said compound(s) of the invention.

For example, said pharmaceutical composition comprises a dose of at least 150 mg and less than 400 mg, and preferably of 200 mg, of said compound(s) of the invention.

According to a preferred embodiment, the compound of the invention is administered for the treatment of severe persistent asthma, and in particular severe persistent corticosteroid-dependent or corticosteroid-resistant asthma, in combination with at least one corticosteroid or other controller medication.

The second corticosteroid or other controller medication is preferably selected from the group consisting of inhaled corticosteroids (especially high-dose inhaled corticosteroids), oral corticosteroids, anti-IgEs, leukotriene modifiers, long-acting inhaled β2-agonists, and sustained-release theophylline; and any combination of these corticosteroid or other controller medication.

The compound(s) of the invention and one or more corticosteroid or other controller medication may be to be administered separately, simultaneously or sequentially in time.

The invention also relates to a tyrosine kinase inhibitor or a mast cell inhibitor, notably as defined above, especially masitinib for use as a medicament or in a pharmaceutical composition for a method as defined in the description.

In another embodiment, the invention also relates to a method of treatment of severe persistent asthma, and in particular severe persistent corticosteroid-dependent or corticosteroid-resistant asthma, in human patients, wherein a tyrosine kinase inhibitor or a mast cell inhibitor, especially masitinib or a pharmaceutically acceptable salt thereof, is administered for the treatment of severe persistent asthma in combination with at least one corticosteroid or other controller medication; for example, high-dose inhaled corticosteroids, oral corticosteroids, anti-IgEs, leukotriene modifiers, long-acting inhaled β2-agonists, or sustained-release theophylline.

Advantageously, in the use or the method above, said patients have severe persistent corticosteroid-dependent or corticosteroid-resistant asthma. Patients according to the invention are those afflicted by severe persistent asthma with $FEV_1 \leq 60\%$ predicted or $PEF \leq 60\%$ of personal best, or GINA-defined severe persistent asthma in accordance to the classification of asthma severity by daily medication regimen and response to treatment.

Pharmaceutically acceptable salts are pharmaceutically acceptable acid addition salts, like for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic, in particular methanesulfonic acid (or mesilate), or aromatic sulfonic acids, for example benzene-, p-toluene- or naphthalene-2-sulfonic acid.

In a preferred embodiment of the above-depicted treatment, the active ingredient masitinib is administered in the form of masitinib mesilate; which is the orally bioavailable mesylate salt of masitinib—CAS 1048007-93-7 (MsOH); $C_{28}H_{30}N_6OS \cdot CH_3SO_3H$; MW 594.76:

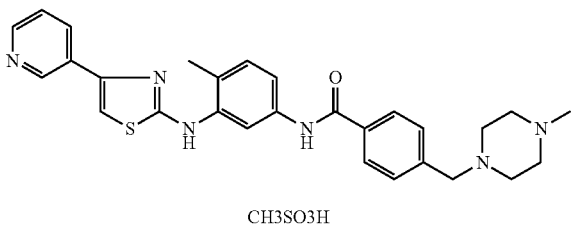 [SMILES: Cc1ccc(NC(=O)c2ccc(CN3CCN(C)CC3)cc2)cc1Nc1nc(-c2cccnc2)cs1 ; "CH3SO3H"]

CH3SO3H

Given that the masitinib dose in mg/kg/day used in the described dose regimens refers to the amount of active ingredient masitinib, compositional variations of a pharmaceutically acceptable salt of masitinib mesilate will not change the said dose regimens.

Masitinib may be administered via different routes of administration but oral administration is preferred. Thus, in still another preferred embodiment, in the use or the method above, masitinib or salts thereof, is administered orally; preferably twice a day for long term period such as over more than 6 months, preferably more than 12 months. Masitinib can be administered in the form of 100 and 200 mg tablets.

According to a particular embodiment, the composition of the invention is an oral composition.

As is known to the person skilled in the art, various form of excipients can be used adapted to the mode of administration and some of them can promote the effectiveness of the active molecule, e.g. by promoting a release profile rendering this active molecule overall more effective for the treatment desired.

The pharmaceutical compositions of the invention are thus able to be administered in various form, more specially for example in an injectable, pulverizable or ingestible form, for example via the intramuscular, intravenous, subcutaneous, intradermal, oral, topical, rectal, vaginal, ophthalmic, nasal, transdermal or parenteral route. A preferred route is oral administration. The present invention notably covers the use of a compound according to the present invention for the manufacture of pharmaceutical composition.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The present invention is illustrated by means of the following examples.

EXAMPLE 1

Clinical Evaluation in Patients with Severe Persistent Asthma

Methods

This was a Phase 2a, 16-week, double-blind, placebo-controlled, randomized, parallel group, multicenter study of daily oral masitinib at doses of 3.0, 4.5, and 6.0 mg/kg/day in asthmatic patients with severe persistent asthma. The objective was to evaluate, in comparison to a placebo, the activity of masitinib, administered orally at three dose levels as assessed by the decrease in oral corticosteroid therapy, asthma control, and clinical and biological safety parameters. The trial consisted of three phases: during the first 4 weeks, the corticosteroid dose remained constant; during the following 8 weeks, oral corticosteroid doses were decreased each week according to a predefined schedule, until weaning or an asthma exacerbation occurred; the final 4 weeks were a stabilization period for observation. Asthma exacerbation was defined as a deterioration of asthma symptoms requiring an emergency visit, a hospitalization or an increase in oral corticosteroid treatment. In case an asthma exacerbation occurred, oral corticosteroid therapy was resumed at the level prior to this occurrence following the acute treatment phase. Patients underwent a visit every 2 weeks during the first 4 weeks, then a weekly visit for the following 12 weeks. A possible treatment extension was part of the study protocol in case of clinical benefit, based on the investigators assessment. In these extension phases the follow-up of patients took place every 4 weeks during the first 3 months and then every 12 weeks until the end of the study.

The primary objective was to measure the reduction of oral corticosteroids doses after 16 weeks of treatment. Therefore, efficacy and safety measurements were assessed at enrolment of each patient in the study prior to the administration of the investigational compound and then at week 2, and weekly from weeks 4 through to 16. The secondary objectives were to monitor the change from baseline in symptomatic scores (asthma control questionnaire, ACQ), the $FEV_1$ and rescue medication intake when necessary.

Patients, 18 to 75 years of age with a diagnosis of asthma for ≥3 years and severe uncontrolled disease for ≥1 year, and followed up at the same centre for ≥1 year, were eligible for this study. Patients were required to have exhibited within 1 year of screening the following characteristics: (a) post-bronchodilator reversibility in forced expiratory volume in one second ($FEV_1$) of ≥12%; (b) to have experienced asthma symptoms more than once in 3 days for ≥3 months before screening despite continuous treatment with high-dose inhaled corticosteroids (beclometasone≥1000 µg or equivalent), long-acting beta2 agonists, and daily oral corticosteroids (10 to 50 mg of equivalent prednisolone, with stable dosage for at least 3 months); and (c) patients had to be non-smokers for at least 1 year with a prior tobacco consumption of <10 pack-years. Exclusion criteria included: (a) any other significant respiratory or cardiac disease; (b) worsening of asthma symptoms requiring treatment with additional oral corticosteroids within 4 weeks of screening; (c) any other infections; (d) a history of acute infection requiring hospitalization or treatment with antibiotics within 2 weeks of screening; (e) rare variants of severe asthma such as Churg-Strauss syndrome or allergic bronchopulmonary aspergillosis; (f) inadequate organ function (total bilirubin >1.5 times the upper limit of normal range, liver transaminases >2.5 times the upper limit of normal range, neutrophil count <2,500/ml and platelet count <150,000/ml at baseline; and (g) concomitant treatments with immuno-modulatory drugs. A treatment wash-out period of 4 months at time of enrolment was required for prior use of omalizumab.

Results

Forty-four patients were included in this study, recruited from 15 centers and randomized in a 3:1 ratio with 33 masitinib-treated subjects (12, 11 and 10 patients received 3.0, 4.5, and 6.0 mg/kg/day, respectively) and 11 placebo-treated subjects (see Table 1). All had poorly controlled severe refractory corticosteroid-dependent asthma with a mean pre-bronchodilator $FEV_1$ of 59±18% of predicted value, a high ACQ score (3.2±1.1) and an average of 5.1±5.0 puffs short-acting beta2 agonists per day. In addition to oral corticosteroids at 23±11 mg equivalent prednisone per day, baseline asthma therapy included high-dose inhaled corticosteroids (2492±1352 µg equivalent beclometasone per day) and long-acting beta2 agonists in 88.6% (see Table 3). Other asthma treatments included leukotriene receptor antagonists and theophylline in 29.5% and 25.0% of patients, respectively. Twenty-five out of the 44 patients received regularly high-dose oral corticosteroids, defined as >15 mg equivalent prednisone per day.

The definition and characteristics of the enrolled subjects in the present trial fulfilled all criteria for patients with severe uncontrolled asthma according to the GINA guidelines 14. Patients were already cared for by experts at specific centers for their disease and accordingly most of the potential confounding factors; including poor compliance with the regimen had been investigated and corrected.

Fourteen patients (31.8%) dropped out prematurely before week 16 (W16), mainly due to adverse events (AE) (57%) or insufficient therapeutic efficacy (14%). The dropout rate was similar in the masitinib and placebo treatment groups. Thirty patients (68.2%) completed the 16-week study period. The different composition of the patient population at baseline between the three masitinib dose groups and the small sample size did not allow any intra-dose comparisons. Nevertheless, no consistent dose-effect relationship was observed throughout the different efficacy endpoints investigated (Table 4). We therefore merged all data and compared masitinib-exposed patients to placebo-treated subjects. As shown in Table 5, patients receiving >15 mg equivalent prednisone per day showed a median percent reduction in oral corticosteroid doses of 52±53% in masitinib-treated patients versus 28±47% in the placebo group (p=0.223), with six patients (31.6%) weaned at W16 in the masitinib treatment groups versus none in the placebo aim (p=0.278). In parallel, the asthma exacerbation rate in patients experiencing at least one exacerbation decreased by 42.4% in the masitinib group compared to 54.5% in the placebo group.

An improved asthma control was observed in masitinib-treated patients. This assertion was reflected in the ACQ score, asthma symptoms and rescue medication intake reported by the patients. ITT analysis showed that masitinib-treated patients improved their ACQ score by 0.99 unit at W16 (p<0.001, see FIGS. 1 and 2). This improvement of asthma control occurred during the stringent procedure of the corticosteroid wean. ACQ score changes were 0.56, 1.57 and 0.89 units in patients treated with 3.0, 4.5, and 6 mg/kg dose, respectively. A non-significant ACQ improvement of 0.43 units at W16 was also observed in the placebo treatment group.

Of all patients treated with masitinib, regardless of dose, 93.9% experienced at least one AE versus 90.9% of the patients enrolled in the placebo treatment group. The most frequent masitinib-related AEs reported were nausea (30.3%), skin rash (30.3%), peripheral edema (18.2%), diarrhea (18.2%), vomiting (12.1%), fatigue (12.1%), and pruritus (12.1%). These AEs were often transient and resolved spontaneously or with adequate treatment. No clear dose relationship could be established regarding event frequency at the exception of skin rash and edema, which showed an increased incidence with the high-dose regimens.

TABLE 3

Baseline demographics, disease characteristics, and concomitant medications

| Parameters | Masitinib groups (mg/kg/day) | | | All masitinib (N = 33) | Placebo (N = 11) | All (N = 44) |
| --- | --- | --- | --- | --- | --- | --- |
| | 3.0 (N = 12) | 4.5 (N = 11) | 6.0 (N = 10) | | | |
| Female, n (%) | 9 (75.0%) | 7 (63.6%) | 7 (70.0%) | 23 (69.7%) | 8 (72.7%) | 31 (70.5%) |
| Age (years) | 55 ± 14 | 49 ± 10 | 51 ± 13 | 52 ± 12 | 58 ± 15 | 53 ± 13 |
| Body Mass Index (kg/m$^2$) | 29 ± 8 | 29 ± 9 | 29 ± 9 | 29 ± 8 | 32 ± 6 | 30 ± 8 |
| Disease duration (years) | 24 ± 18 | 21 ± 14 | 29 ± 13 | 24 ± 15 | 18 ± 18 | 23 ± 16 |
| Time since last exacerbation (months) | 4 ± 2 | 4 ± 2 | 7 ± 11 | 5 ± 6 | 6 ± 9 | 5 ± 7 |
| Pre-bronchodilator $FEV_1$ (% of predicted) | 51.9 ± 11.1 | 67.4 ± 10.8 | 60.6 ± 17.1 | 59.7 ± 14.3 | 58.9 ± 27.3 | 59.5 ± 18.1 |
| ACQ score (1-7 scale) | 2.8 ± 0.8 | 3.6 ± 1.1 | 3.1 ± 1.5 | 3.2 ± 1.1 | 3.4 ± 1.2 | 3.2 ± 1.1 |
| OCS (equivalent prednisone mg/day) | 25 ± 11 | 22 ± 12 | 26 ± 12 | 24 ± 11 | 19 ± 11 | 23 ± 11 |
| ICS, (equivalent beclometasone (µg/day) | 1690 ± 1110 | 2850 ± 1376 | 3000 ± 1224 | 2470 ± 1340 | 2556 ± 1460 | 2492 ± 1352 |
| SABA (number of puffs/day) | 4.7 ± 3.8 | 3.6 ± 3.9 | 6.4 ± 7.8 | 5.0 ± 5.4 | 5.5 ± 3.7 | 5.1 ± 5.0 |
| Other Concomitant asthma medications | | | | | | |
| Long-acting beta2 agonist, n (%) | 10 (83.3%) | 10 (90.9%) | 10 (100.0%) | 30 (90.9%) | 9 (81.8%) | 39 (88.6%) |

TABLE 3-continued

Baseline demographics, disease characteristics, and concomitant medications

| Parameters | Masitinib groups (mg/kg/day) | | | All masitinib (N = 33) | Placebo (N = 11) | All (N = 44) |
|---|---|---|---|---|---|---|
| | 3.0 (N = 12) | 4.5 (N = 11) | 6.0 (N = 10) | | | |
| Leukotriene modifiers, n (%) | 4 (33.3%) | 4 (36.4%) | 3 (30.0%) | 11 (33.3%) | 2 (18.2%) | 13 (29.5%) |
| Theophylline, n (%) | 3 (25.0%) | 1 (9.1%) | 3 (30.0%) | 7 (21.2%) | 4 (36.4%) | 11 (25.0%) |

ACQ, Asthma Control Questionnaire;
CS, corticosteroids;
$FEV_1$, Forced Expiratory Volume in 1 Second;
ICS, Inhaled Corticosteroids;
OCS, Oral Corticosteroids;
SABA, Short-acting beta2 agonist;
all values are Mean ± SD, Standard deviatio

TABLE 4

Oral corticosteroids wean (ITT population)

| Parameters | Masitinib groups (mg/kg/day) | | | All masitinib (N = 33) | Placebo (N = 11) |
|---|---|---|---|---|---|
| | 3.0 (N = 12) | 4.5 (N = 11) | 6.0 (N = 10) | | |
| Absolute change (W 4 to W 16) | | | | | |
| Mean ± SD | −10.7 ± 19.2 | 0.2 ± 26.8 | −12.2 ± 18.5 | −8.0 ± 21.3 | −7.0 ± 11.7 |
| Median | −14.0 | −7.5 | −11.3 | −12.3 | −10.0 |
| Q1; Q3 | −20; −10 | −12.5; −2.5 | −25; −2.5 | −20; −5 | −10; 0 |
| Min; Max | −32.5; 45.0 | −18.8; 65.0 | −40.0; 20.0 | −40.0; 65.0 | −25.0; 20.0 |
| Relative change (W 4 to W 16) | | | | | |
| Mean ± SD | −41 ± 113 | 2 ± 179 | −46 ± 69 | −30 ± 123 | −49 ± 50 |
| Median | −82 | −56 | −69 | −78 | −57 |
| Q1; Q3 | −100; −33 | −97; −6 | −100; −17 | −100; −19 | −100; 0 |
| Min; Max | −100; 300 | −100; 433 | −100; 100 | −100; 433 | −100; 50 |
| Patients weaned at W 16 | 5 (41.7%) | 2 (25.0%) | 3 (37.5%) | 10 (35.7%) | 3 (27.3%) |

TABLE 5

Oral corticosteroids wean (subpopulation initially treated with >15 mg prednisone daily/ITT population)

| Parameters | Masitinib groups (mg/kg/day) | | | All masitinib (N = 19) | Placebo (N = 6) |
|---|---|---|---|---|---|
| | 3.0 (N = 9) | 4.5 (N = 4) | 6.0 (N = 6) | | |
| Absolute change (W 4 to W 16) | | | | | |
| Mean ± SD | −17 ± 9 | −7 ± 8 | −14 ± 22 | −14 ± 14 | −7 ± 16 |
| Median | −20 | −5 | −16 | −15 | −8 |
| Q1; Q3 | −20; −13 | −12; −3 | −30; 0 | −20; −5 | −20; 0 |
| Min; Max | −33; 0 | −19; 0 | −40; 20 | −40; 20 | −25; 20 |
| Percent change (W 4 to W 16) | | | | | |
| Mean ± SD | −68 ± 38 | −33 ± 42 | −40 ± 78 | −52 ± 53 | −28 ± 47 |
| Median | −81 | −19 | −69 | −65 | −38 |
| Q1; Q3 | −100; −33 | −59; −6 | −100; 0 | −100; −13 | −57; 0 |
| Min; Max | −100; 0 | −94; 0 | −100; 100 | −100; 100 | −83; 50 |
| Patients weaned at W 16 | 4 (44.4%) | 0 (0.0%) | 2 (33.3%) | 6 (31.6%) | 0 (0.0%) |

FIG. 1: Mean absolute change in ACQ score (0-7 items), according to treatment group (ITT population). Symbols: *=3 mg/kg; Δ=4.5 mg/kg, □=6 mg/kg for the treatment groups, ◆=masitinib combined, and o=placebo group.

Discussion

In a small group of well-characterized patients, masitinib was able to improve asthma control, as evidenced by ACQ and frequency of severe exacerbations, whilst at the same time reducing the patient dependence of oral corticosteroid therapy. As is true for other studies in severe asthma, including agents recently approved for the management of such patients, there was no significant change in lung function in this trial. The significant benefit observed in the masitinib-treated patients on the control of their disease is comparable to the effect observed in previous studies of other drugs in less severe asthma populations. Improvement in asthma control has been rarely reported in severe asthmatic patients to date, indicating the potential interest of masitinib in the population studied. This response was achieved with some mild-to-moderate and transient drug-related AEs, which were mainly cutaneous and gastro-intestinal.

The improvement in asthma control for masitinib-treated patients reached the minimal clinically important change as described by the ACQ score. Exacerbations are a common manifestation in patients with poorly controlled severe asthma, and are associated with an increased risk of mortality. In the present study, the rate of asthma exacerbation was significantly reduced in the masitinib-treated patients as compared to placebo. This parameter is relevant as exacerbations are common and contribute to the burden linked to severe asthma. Of note, omalizumab therapy was approved for the treatment of severe, difficult-to-control allergic asthma, based on an improved exacerbation rate in a population with severe asthma [Humbert M, et al., Allergy 2005; 60:309-16] highlighting the possible importance of masitinib in severe asthma.

Figure 2:
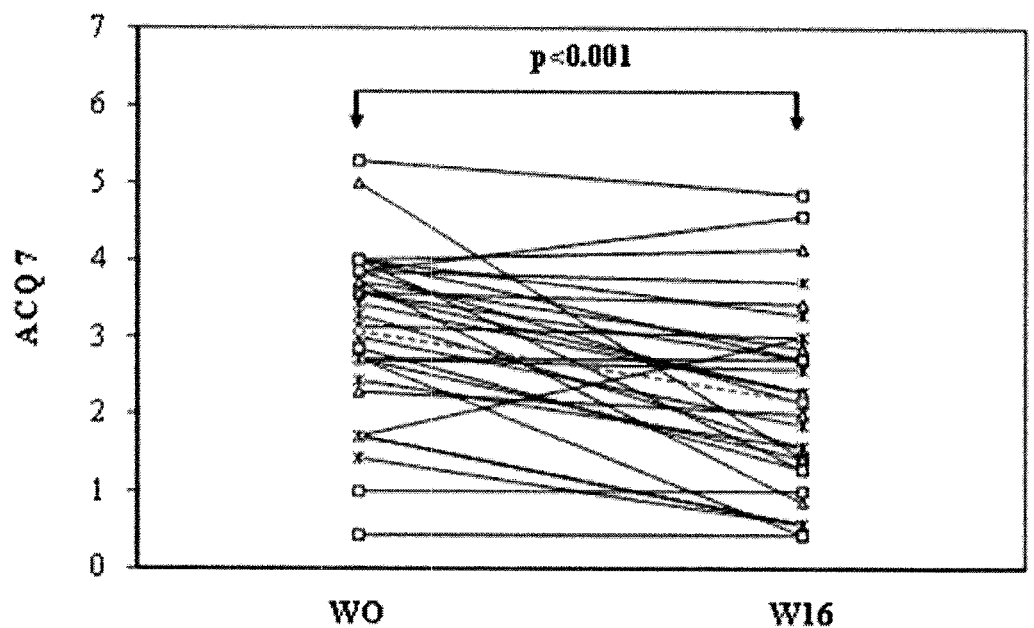
Figure 2:
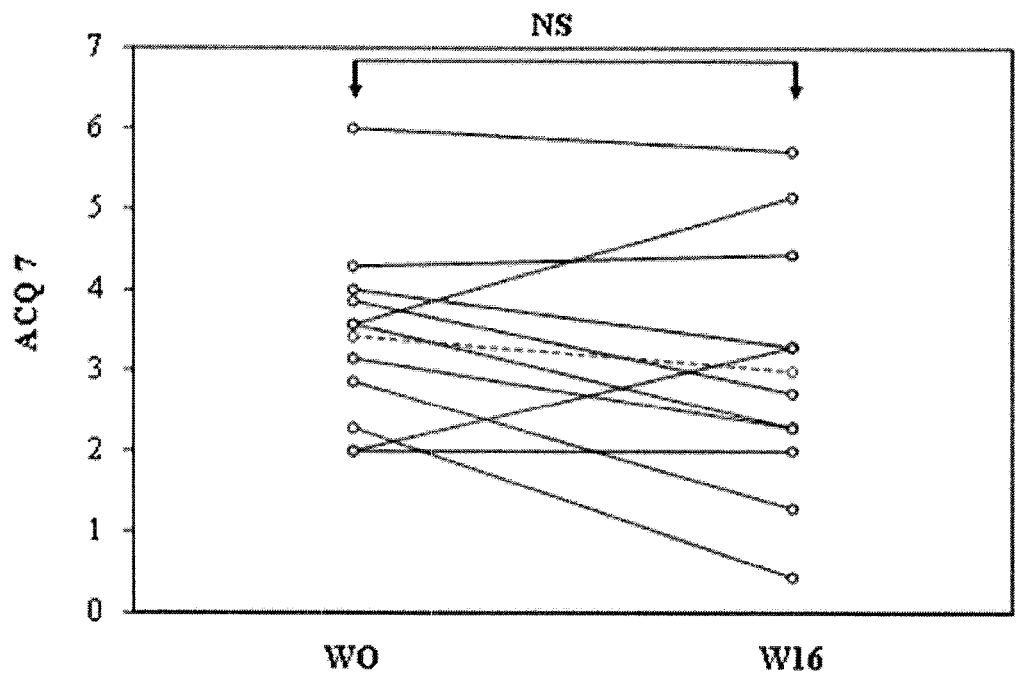

FIG. 2: Absolute change in ACQ score, according to the ITT population. Upper panel: masitinib treatment group. Lower panel: placebo group. NS=non-significant, symbols: *=3 mg/kg; Δ=4.5 mg/kg, □=6 mg/kg for the treatment groups and o=placebo group. The red dashed line gives the median improvement over the period of 4 months.

The decreased use of systemic corticosteroid observed in the placebo population indicated that their corticosteroid dosage had not been optimized; a commonly reported occurrence in other asthma corticosteroid-dependent trials with no run-in phase for ensuring minimal dosing levels of oral corticosteroid. To account for this possible confounding effect, a subgroup analysis was performed in patients receiving a high daily dose of corticosteroids (>15 mg) at baseline. In those patients, doses of oral corticosteroids were reduced by 52±53% in masitinib-treated patients versus 28±47% in the placebo group and six patients were weaned off oral corticosteroids at W16 in the masitinib treatment groups versus none in the placebo group.

In conclusion, this proof-of-concept study showed that masitinib improved asthma control by alleviating daily symptoms and reducing asthma exacerbations while concomitantly reducing systemic exposure to corticosteroids. Given masitinib's highly specific tyrosine kinase inhibition profile and ability to lower the burden and activity of mast cells, these observations suggest that c-Kit, Lyn and PDGFR inhibition should be considered as a potential targets for treatment of severe asthma. Masitinib therefore represents an innovative avenue of treatment in corticosteroid-dependent asthma and has the potential to serve as an effective long-term treatment for severe asthma.

EXAMPLE 2

Evaluation Masitinib for Treatment of Experimental Feline Asthma

Introduction

Similar to human asthma, feline allergic asthma is a common clinical disease that is typically treated with corticoids and bronchodilators. Both oral and inhaled corticoids have been shown to be efficacious in controlling eosinophilic airway inflammation in experimental models of feline allergic asthma. However, corticoids can be associated with adverse effects and may be relatively contraindicated with certain infectious, cardiac or endocrine diseases. Regular use of the inhaled bronchodilator albuterol as monotherapy in experimentally asthmatic cats has been shown to exacerbate eosinophilic airway inflammation. Other bronchodilators, while they modulate airflow limitation, do not adequately control airway inflammation, which can exacerbate airway hyper-reactivity and progress to airway remodeling. Therefore, the search for novel, efficacious, and safe treatments with the potential to ameliorate both airway inflammation and airflow limitation is ongoing. This study tests the hypothesis that masitinib would be effective in this study population at decreasing eosinophilic airway inflammation and blunting airway hyper-reactivity with acceptable toxicity.

Materials and Methods

Twelve experimentally asthmatic cats were enrolled in a randomized, blinded, placebo-controlled study. Cats were enrolled if they met the following inclusion criteria: weight of at least 3.5 kg, % bronchoalveolar lavage fluid (BALF) eosinophils>17% after allergen sensitization and challenge, hemoglobin>10 g/dL, platelets>100×103/μL, AST<3× upper limit normal (ULN), ALT<3×ULN, bilirubin<1.5×ULN, albumin>lower limit normal, creatinine<ULN, urine specific gravity>1.040, and urine dipstick protein<30 mg/dL or urine protein:creatinine ratio (UPC)<1. Exclusion criteria were evidence of cardiac insufficiency, evidence of gastric bleeding, major surgery within 2 weeks of treatment initiation, life expectancy less than 3 months, lactating or pregnant cats or cats intended for breeding, previous history of kidney disease or previous known episodes of proteinuria, administration of food listed on the "recall list" issued by FDA or vaccination within 4 weeks prior to enrollment, and any concurrent medical illness. Cats were subsequently randomized to receive 50 mg masitinib or placebo tablets (both identical in appearance and provided by AB Science, Paris, France) orally once daily with food over the study duration of 12 weeks.

Bronchoalveolar lavage fluid (BALF) eosinophil percentages and airway hyper-reactivity, determined by changes in ventilator mechanics in response to methacholine (MCh) challenge were evaluated at baseline, weeks 4, 8 and 12. Results of the MCh challenge were reported as the effective concentration of MCh that increased baseline airway resistance by 200% (EC200Raw) and the end-inspiratory pressure after a breath hold (plateau pressure, Pplat). Treatment was interrupted or discontinued if predetermined adverse events were noted.

Cats naïve to Bermuda grass allergen (BGA) confirmed by intradermal skin testing (IDST) and with normal BALF underwent allergen sensitization. IDST was re-evaluated to confirm allergen sensitization. Next, allergen challenge of BGA as an aerosol in awake, spontaneously breathing cats was performed. Allergen solution (100 μg of BGA dissolved in PBS) was aerosolized into a clear chamber using an air compressor attached to a nebulizer. Seven challenges were administered over the next 2 weeks, at which time BALF was repeated to confirm development of eosinophilic airway inflammation. Bronchoalveolar lavage fluid was collected in a blind fashion at baseline and weeks 4, 8, and 12 of the study. Collection of BALF was obtained after Mch challenge and under the same anesthesia. A total nucleated cell count was performed on each BALF sample using a coulter counter. Cytological evaluation and differential cell counts were performed on samples prepared by cytocentrifugation. Differential cell counts (200 nucleated cells per slide) on modified Wright's stained slides were performed, and cell percentages were reported.

Results

Bronchoalveolar Lavage Fluid (BALF) Eosinophil Percentages and Airway Hyperreactivity All cats were available for evaluation at baseline and week 4; at weeks 8 and 12 there was attrition due to adverse events and thus, statistical analyses were not performed at these later time points. There was no significant difference in the baseline group mean±SD % BALF eosinophils between treatment groups prior to the start of the study (masitinib, 46±24%; placebo, 44±22%; p=0.345). After 4 weeks of therapy, the group mean±SD % BALF eosinophils was significantly lower in masitinib-treated cats compared with placebo-treated cats (masitinib, 7±9%; placebo 30±27%; p=0.023). The % BALF eosinophils was <17% in five of six masitinib-treated cats at week 4 (values at 1%, 1%, 2%, 3.5% and 15%) consistent with a non-asthmatic (or well controlled asthmatic) phenotype. There was no significant difference in the group mean±SD EC200Raw between groups at baseline or after 4 weeks of therapy. However, after 4 weeks of therapy, the Pplat with MCh challenge significantly (p=0.016) increased in placebo-treated but not masitinib-treated cats (p=0.32), reflecting a blunting of airflow limitation in the latter group. The Pplat for individual cats after saline aerosol compared to Pplat after MCh challenge at baseline and week 4 is shown in FIG. 3.

Figure 4:
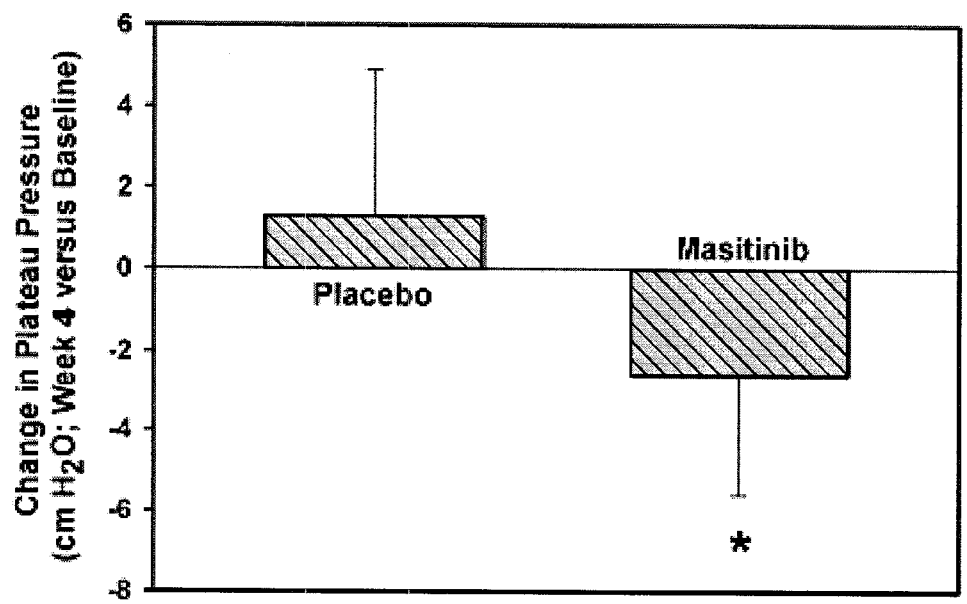

When the change in Pplat with MCh challenge versus saline aerosol was compared between the two treatment groups, there was a significant (p=0.033) decrease in the masitinib-treated cats indicative of a blunting of bronchoprovocant-induced airflow limitation (FIG. 4).

Figure 3:
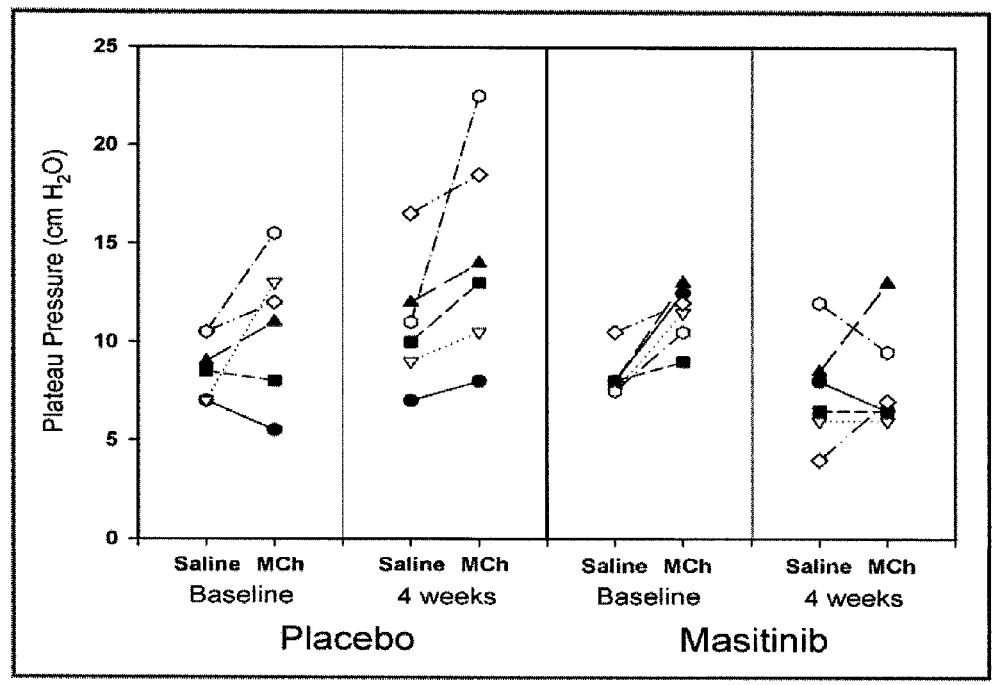

FIG. 3 Plateau pressure (Pplat) after saline and after bronchoprovocation with methacholine (MCh) in individual cats before (i.e., baseline) and after 4 weeks of treatment with placebo (n=6) or masitinib (n=6). Increased Pplat after MCh challenge, reflective of airflow limitation, was seen in placebo-treated but not masitinib-treated cats at week 4 of study.

FIG. 4 Changes in the Pplat difference (maximum Mch—saline) comparing week 4 to baseline for placebo-(n=6) and masitinib-treated (n=6) cats. * Denotes a significant (p=0.033) decrease in the Pplat difference in masitinib-treated cats compared with placebo-treated cats. Values represent mean±SD.

Safety and Tolerability

The major adverse reaction noted in this study was proteinuria, which was detected in every cat receiving 50 mg/day of masitinib. Masitinib-treated cats were significantly more likely to develop proteinuria than placebo-treated cats (p=0.002). This led to temporary drug interruption followed by dose reduction in two cats and permanent discontinuation in four cats at or after week 4 and precluded meaningful statistical analysis at weeks 8 and 12. However, even if severe (e.g., UP:C>10), the proteinuria was self-limiting after discontinuation of masitinib; additionally, the cats displayed no outward chronic clinical signs of illness. Other side effects suspected of being associated with masitinib administration were vomiting, diarrhea, Heinz bodies, hypoalbuminemia, hypoglobulinemia, hypercholesterolemia and ALT increase; additionally there was one cat with a decreasing hematocrit that was not overtly anemic. These adverse events were infrequent overall and did not require specific therapy.

Discussion and Conclusions

This is the first study to show that the TM masitinib significantly reduces eosinophilic airway inflammation and decreases one measure of airway hyper-reactivity (Pplat) after 4 weeks of administration in experimentally asthmatic cats. Pplat is a measure of airway resistive pressures which correlates with airway resistance changes from increased intraluminal secretions, airway wall inflammation or bronchoconstriction. It is expected that Pplat should increase after MCh challenge in comparison to the Pplat obtained after saline challenge if airflow limitation is induced by MCh. In placebo-treated cats at week 4, there was a significant increase in Pplat after MCh challenge; this was not noted in masitinib-treated cats at the same time point. In other words, masitinib blunted the bronchoconstrictive response to MCh and was a more sensitive parameter of airway hyper-reactivity than the EC200Raw.

Eosinophilic airway inflammation is one of the major features of feline allergic asthma and can contribute both to airway hyper-reactivity and remodeling. Therefore, reducing inflammation is a key objective for slowing the progression of disease. Additionally, airway hyper-reactivity enhances the susceptibility to bronchospasm and subsequent clinical symptoms in human asthmatics, and as such is also an important target of therapy. Masitinib thus represents a novel treatment with the potential to impact both of these key components of asthma pathogenesis in cats.

EXAMPLE 3

Evaluation of Masitinib in the Murine Model of Allergic Airway Inflammation

Methods

The ability and effect of masitinib to inhibit mast cell function in asthma was explored in a classical murine model of allergic airway inflammation. Balb/c male mice aged 9 weeks were sensitized with ovalbumine (50 μg) adsorbed with Al(OH)3 diluted in physiological saline (0.9% NaCl) by intraperitoneal injection on day 1 and 7. Sensitization was followed by intranasal challenges with ovalbumine (10 μg) diluted in 0.9% NaCl every day from day 18 to day 21. Non sensitized control animals received intraperitoneal injections of vehicle alone followed by intranasal challenges with NaCl 0.9% alone at the same time than the sensitized animals. On days 17 to 21, animals were daily dosed with 25 or 100 mg/kg/day masitinib.

On day 22, airway hyper responsiveness (AHR) was measured by the enhanced pause (PenH) in the whole body plethysmograph. The bronchoconstrictive response was evaluated as the response to a concentration-dependent methacholine (MCh) aerosol exposure. Mice were first exposed to a saline aerosol then to an aerosol generated from increasing concentrations of methacholine (0.05, 0.1, 0.2, 0.3, and 0.4M). Infiltration of inflammatory cells was measured immediately after assessment of AHR to methacholine via collection of bronchoalveolar lavage (BAL) fluid by lavage of the whole lung with physiological saline containing 1.6 mM EDTA. Cells were counted in the BAL and cell types identified by morphological criteria after Hemacolor staining.

Results

Figure 5:
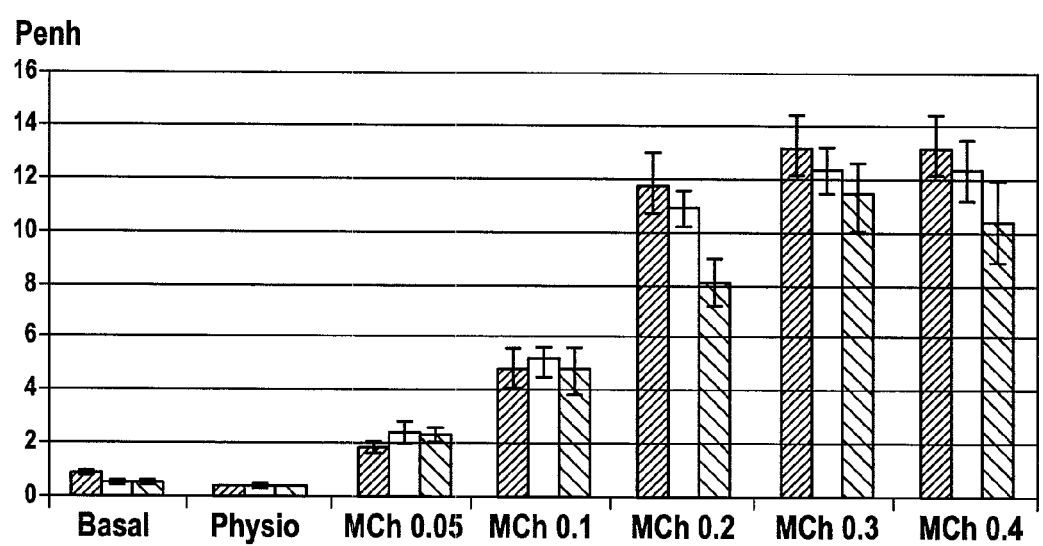
Figure 6:
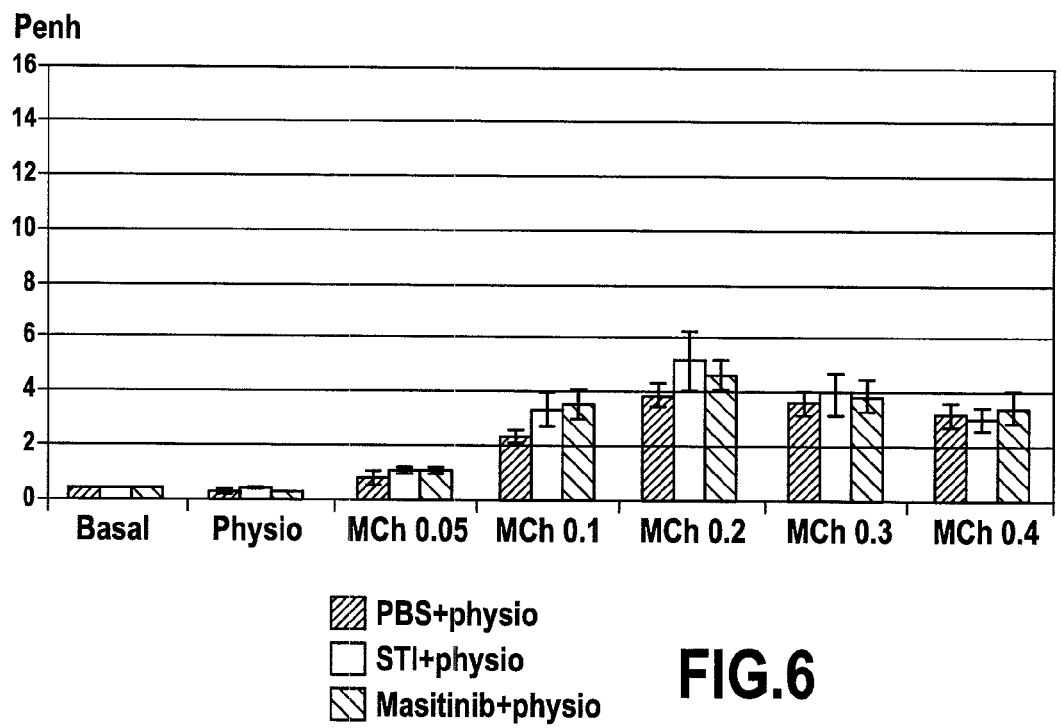
Figure 7:
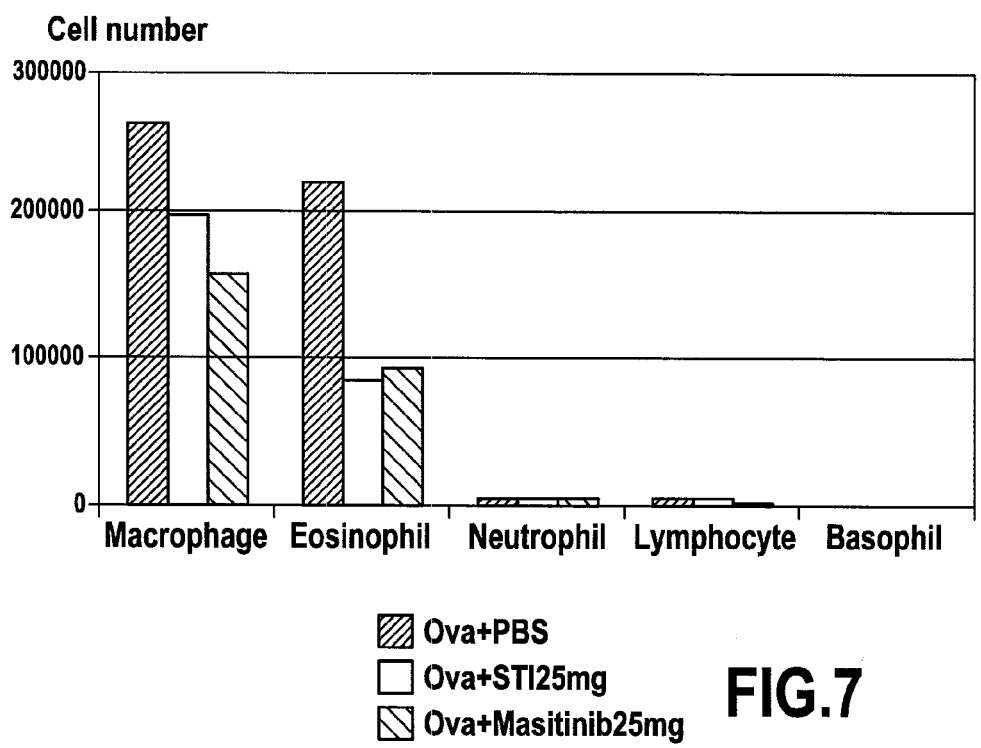

Results for the effect of masitinib on the AHR of mice are shown in FIGS. 5 and 6. Results for the effect of masitinib on the number of inflammatory cells in BAL of mice are shown in FIG. 7. After oral administration, masitinib twice daily at doses of 25 and 100 mg/kg/day (not presented) induced a marked decrease in the number of eosinophils in the bronchoalveolar lavage fluid of sensitized and challenged animals, and a decrease of Penh. There was no clear dose-effect observed in this model.

FIG. 5: Effect of masitinib on the airway hyper responsiveness of mice according to enhanced pause (PenH) index of airway hyper-reactivity. Ovalbumine Reactivity.

MCh=Methacholine (molar). Physio=physiological saline. Ova=ovalbumine. STI=Imatinib (STI571).

FIG. 6: Effect of masitinib on the airway hyper responsiveness of mice. Non Specific Reactivity.

MCh=Methacholine (molar). Physio=physiological saline. STI=Imatinib (STI571).

FIG. 7: Effect of masitinib on the number of eosinophils in bronchoalveolar lavage of mice (n=12).

Ova=ovalbumin. STI=Imatinib (STI571).

In summary, pre-clinical finding and preliminary clinical results validate the relevance of a tyrosine kinase inhibitor, and especially a c-Kit inhibitor targeting mast cell in severe asthma.

The invention claimed is:

1. A method for the treatment of severe persistent asthma in human patients comprising the step of administering a tyrosine kinase inhibitor or a mast cell inhibitor to the human patient, the tyrosine kinase inhibitor or mast cell inhibitor further comprising masitinib or a pharmaceutically acceptable salt thereof.

2. The method according to claim 1, wherein said patients are afflicted by severe persistent asthma with GINA-defined severe persistent asthma in accordance to the classification of asthma severity by daily medication regimen and response to treatment, or with $FEV_1 \leq 60\%$ predicted or $PEF \leq 60\%$ of personal best.

3. The method according to claim 1, wherein said tyrosine kinase inhibitor or a mast cell inhibitor is to be administered for the treatment of severe persistent corticosteroid-dependent asthma.

4. The method according to claim 1, wherein said tyrosine kinase inhibitor or a mast cell inhibitor is to be administered for the treatment of severe persistent corticosteroid-resistant asthma.

5. The method according to claim 1, wherein said tyrosine kinase inhibitor or a mast cell inhibitor is masitinib mesilate.

6. The method according to claim 1, wherein the masitinib is to be administered at a starting daily dose of 3.0 to 6.0 mg/kg/day.

7. The method according to claim 6, wherein masitinib is to be administered at a starting daily dose of 4.5 to 6.0 mg/kg/day.

8. The method according to claim 1, wherein masitinib is dose escalated by increments of 1.5 mg/kg/day to reach a maximum of 9.0 mg/kg/day.

9. The method according to claim 1, wherein said tyrosine kinase inhibitor or mast cell inhibitor is administered orally.

10. The method according to claim 1, wherein said tyrosine kinase inhibitor or mast cell inhibitor is administered twice a day.

11. The method according to claim 1 comprising administering said tyrosine kinase inhibitor or mast cell inhibitor in an effective amount over more than 3 months.

12. The method according to claim 1 comprising administering said tyrosine kinase inhibitor or mast cell inhibitor in an effective amount over more than 12 months.

13. The method according to claim 1, wherein said medicament comprises a dose of at least 50 mg and less than 150 mg of said tyrosine kinase inhibitor or mast cell inhibitor.

14. The method according to claim 1, wherein said medicament comprises a dose of at least 150 mg and less than 400 mg of said tyrosine kinase inhibitor or mast cell inhibitor.

15. The method according to claim 1 wherein the tyrosine kinase inhibitor or a mast cell inhibitor is administered in combination with at least one corticosteroid or other controller medication.

16. The method according to claim 1 wherein the second controller medication is selected from the group consisting of: high-dose inhaled corticosteroids, oral corticosteroids, anti-IgEs, leukotriene modifiers, long-acting inhaled β2-agonists, or sustained-release theophylline.

17. The method according to claim 1 wherein said tyrosine kinase inhibitor or mast cell inhibitor and one corticosteroid or other controller medication are to be administered separately, simultaneously or sequentially in time.

* * * * *